(12) United States Patent
McCamish et al.

(10) Patent No.: US 7,278,975 B2
(45) Date of Patent: Oct. 9, 2007

(54) METHOD AND APPARATUS FOR DETECTING A TREMOR INDUCED IN A SUBJECT

(75) Inventors: Mark Anthony McCamish, Simi Valley, CA (US); Robert Rex Rice, Simi Valley, CA (US)

(73) Assignee: The Boeing Company, Chicago, IL (US)

( * ) Notice: Subject to any disclaimer, the term of this patent is extended or adjusted under 35 U.S.C. 154(b) by 351 days.

(21) Appl. No.: 10/462,336

(22) Filed: Jun. 16, 2003

(65) Prior Publication Data

US 2004/0254502 A1 Dec. 16, 2004

(51) Int. Cl.
- A61B 5/103 (2006.01)
- A61B 5/117 (2006.01)

(52) U.S. Cl. .................. 600/587; 600/306; 600/554
(58) Field of Classification Search ................. 600/306, 600/382, 407, 552, 554, 587
See application file for complete search history.

(56) References Cited

U.S. PATENT DOCUMENTS

| | | | | |
|---|---|---|---|---|
| 4,166,454 A | * | 9/1979 | Meijer | 600/479 |
| 4,358,118 A | * | 11/1982 | Plapp | 463/7 |
| 4,683,891 A | * | 8/1987 | Cornellier et al. | 600/301 |
| 4,817,628 A | * | 4/1989 | Zealear et al. | 600/554 |
| 5,131,401 A | * | 7/1992 | Westenskow et al. | 600/554 |
| 5,507,291 A | * | 4/1996 | Stirbl et al. | 600/407 |
| 5,573,011 A | * | 11/1996 | Felsing | 600/595 |
| 5,797,854 A | * | 8/1998 | Hedgecock | 600/554 |
| 5,847,816 A | | 12/1998 | Zediker et al. | |
| 5,862,803 A | * | 1/1999 | Besson et al. | 600/508 |
| 5,865,167 A | * | 2/1999 | Godik | 600/310 |
| 5,867,257 A | | 2/1999 | Rice et al. | |
| 6,067,468 A | * | 5/2000 | Korenman et al. | 600/547 |
| 6,190,314 B1 | * | 2/2001 | Ark et al. | 600/300 |
| 6,656,116 B2 | * | 12/2003 | Kim et al. | 600/300 |
| 6,854,879 B2 | * | 2/2005 | Pavlidis | 374/45 |

* cited by examiner

*Primary Examiner*—Max Hindenburg
*Assistant Examiner*—Rene Towa
(74) *Attorney, Agent, or Firm*—Alston & Bird LLP

(57) ABSTRACT

A method and apparatus are provided for detecting tremors induced in a subject that are indicative of stress, emotion, fatigue, deception or other similar psychological states. The apparatus includes a signal source for directly applying an excitation signal having a predefined amplitude and frequency to the subject so as to induce the tremor. The apparatus also includes a Doppler system for irradiating the subject with electromagnetic radiation and for detecting the electromagnetic radiation returning from the subject following modulation by the induced tremor. The Doppler system also analyzes the returning electromagnetic radiation to determine at least one of an amplitude of the induced tremor and a phase shift of the induced tremor relative to the excitation signal provided by the signal source. The amplitude and/or phase shift of the modulated electromagnetic radiation provide information regarding the stress, emotion, fatigue, deception or other similar psychological states of the subject.

7 Claims, 2 Drawing Sheets

METHOD AND APPARATUS FOR DETECTING A TREMOR INDUCED IN A SUBJECT

FIELD OF THE INVENTION

The present invention relates generally to the detection of the stress, emotion, fatigue, deception or other similar psychological states of a subject and, more particularly, to a method and apparatus for detecting a tremor induced in a subject that provides information relating to the stress, emotion, fatigue, deception or other similar psychological states of the subject.

BACKGROUND OF THE INVENTION

It is oftentimes desirable to determine the psychological state of a subject. For example, it may be desirable to determine if a subject is under stress, fatigued, attempting to deceive or is otherwise experiencing a particular psychological state. For example, it may be desirable to evaluate the veracity of a subject's statements so as to identify instances in which a subject is lying or is otherwise attempting to deceive.

In this regard, an instrument for detecting and measuring physiological changes such as increased pulse rate, muscle tremor, perspiration and subdermal blood flow, that accompany emotional stress, such as the stress created by attempts to deceive, is commonly referred to as a polygraph. A polygraph typically includes multiple sensors that are directly connected to a subject for measuring multiple physiological parameters. Standard polygraph sensors include a blood pressure cuff, a pair of respiration belts, and skin resistance finger electrodes for measuring pulse rate, respiration rate and the galvanic skin response (GSR) of the subject, respectively. All of these physiological parameters are generally coupled to data collection and recordation equipment.

GSR reflects the emotional stress level of the subject by providing a measure of skin conductivity or resistance, which is largely influenced by sweat gland activity. The sweat glands secrete perspiration that flows to the surface of the skin. The perspiration includes liquid and electrolytes; therefore, perspiration facilitates electrolytic conduction at the surface of the skin. GSR testing typically includes attaching electrodes to separate fingers of the same hand and attaching a galvanometer to the electrodes to measure the conductance or resistance between the electrodes.

Having to attach electrodes to a subject to measure their GSR can be disadvantageous in some circumstances. The electrodes are invasive, and therefore they can be uncomfortable to the subject and can themselves cause the individual being tested to become stressed. The invasive and stressful nature of conventional GSR testing can disadvantageously contribute to people's hesitance to be subjected to GSR and polygraph examinations, and to some degree also complicates the interpretation of the results of such examinations. Moreover, a conventional polygraph is not readily portable, is difficult to use, requires a highly trained operator and is not always trustworthy.

Another conventional technique for detecting stress, emotion, fatigue, deception or other similar psychological states of a subject utilizes functional magnetic resonance imaging (MRI). An MRI technique detects metabolic activity in neural tissue and provides corresponding three dimensional images with those regions of the neural tissue exhibiting metabolic activity being indicated or highlighted. The equipment required for an MRI examination, however, is quite expensive and the conduct of an MRI examination may again cause a subject to be uncomfortable and create additional stress for the subject, thereby complicating the interpretation of the images created by the MRI examination.

In addition to generally detecting stress and, more particularly, detecting the stress attributable to efforts by the subject to deceive, it may sometimes also be desirable to detect other psychological states, such as fatigue. For example, it would be desirable to determine if personnel that perform certain critical functions, such as air traffic control or other flight operations functions, were becoming fatigued since the fatigue, in turn, could lead to the degradation of their performance. Likewise, with the elevated concerns regarding terrorism, it would be desirable to reliably evaluate subjects, preferably in a relatively rapid manner, to determine if the subjects are experiencing stress or other emotions that may be indicative of their intent to commit a terrorist act. To date, however, the techniques utilized to detect and measure the physiological changes that accompany stress, such as polygraph and MRI techniques, are not readily scalable and generally require a highly trained and skilled technician to administer and/or interpret the results.

As such, it would be desirable to provide an improved technique for detecting stress, emotion, fatigue, deception or other similar psychological states of a subject. In this regard, it would be desirable to provide a method and apparatus for detecting stress, emotion, fatigue, deception or other similar psychological states of a subject in a manner that is reliable, relatively non-invasive, relatively inexpensive and can be performed in a rapid manner by an operator that need not have extensive training to administer the test and/or interpret the results.

BRIEF SUMMARY OF THE INVENTION

A method and apparatus are therefore provided for detecting tremors induced in a subject that are indicative of stress, emotion, fatigue, deception or other similar psychological states of the subject. The method and apparatus of the present invention therefore provide a reliable technique for detecting emotional stress experienced by a subject in a less expensive and less invasive manner than conventional techniques. Moreover, the method and apparatus of the present invention can be practiced in an efficient manner by an operator who need not be as highly trained as those required to operate conventional polygraph and MRI devices.

According to one aspect of the present invention, an apparatus for detecting a tremor induced in the subject is provided that includes a signal source for providing an excitation signal having a predefined amplitude and frequency. The signal source directly applies the excitation signal to the subject so as to induce the tremor. In one embodiment, the signal source is an electrical signal source for providing electrical stimulus to the subject. Typically, the frequency of the electrical stimulus is no more than 100 Hz. However, the signal source may be configured such that the excitation signal has a controllably adjustable frequency, thereby permitting the excitation signal applied to the subject to be scanned over a range of frequencies and/or permitting the excitation signals applied to different subjects to have different frequencies tailored to the respective subjects.

In order to apply the electrical stimulus to the subject, the signal source of one embodiment may also include electrodes affixed to the subject. In addition to applying the electrical stimulus, a detector may be disposed in electrical communication with the electrodes for determining the GSR of the subject.

The apparatus of this aspect of the present invention also includes a Doppler system for irradiating the subject with electromagnetic radiation and for detecting the electromagnetic radiation returning from the subject. In this regard, the Doppler system may comprise a laser Doppler system having a laser transmitter for providing electromagnetic radiation to irradiate the subject and a laser receiver for receiving electromagnetic radiation returning from the subject following modulation by the induced tremor. The Doppler system also advantageously analyzes the returning electromagnetic radiation. In this regard, the Doppler system and, more commonly, a signal processor that is responsive to or at least partially embodied by the laser receiver determines at least one of an amplitude of the induced tremor and a phase shift of the induced tremor relative to the excitation signal provided by the signal source. In this regard, the laser receiver may include a phase sensitive receiver for detecting the phase shift of the induced tremor relative to the excitation signal provided by the signal source. In one embodiment, the phase sensitive receiver is a phase locked loop for phase locking the excitation signal provided by the signal source to the induced tremor.

In operation, an excitation signal, such as an electrical stimulus, is applied to the subject to induce a tremor. While the excitation signal is applied to the subject, the subject is irradiated with electromagnetic radiation. Thus, the modulated electromagnetic radiation returning from the subject may be detected and analyzed so as to monitor the induced tremor. In this regard, the amplitude of the returning electromagnetic radiation may be detected. Additionally, or alternatively, the returning electromagnetic radiation may be analyzed to determine a phase shift of the induced tremor relative to the electrical stimulus applied to the subject. While the returning electromagnetic radiation may be analyzed quantitatively, the returning electromagnetic radiation may also be compared to a pre-established baseline so as to detect any meaningful variations therefrom which may be indicative of stress, emotion, fatigue, deception or other similar psychological states.

In embodiments in which an electrical stimulus is applied to the subject, an electrical stimulus having a predefined amplitude and frequency may be applied, although the frequency of the electrical stimulus may be varied, in a predefined manner, if so desired. Typically, however, the frequency of the electrical stimulus is no greater than 100 Hz. In addition to applying the electrical stimulus to the subject, such as by means of a pair of electrodes, the galvanic skin response of the subject may be determined and analyzed, typically in concert with the analysis of the modulated returning electromagnetic radiation.

Accordingly, the method and apparatus of the present invention provide a cost effective technique for reliably detecting stress, emotion, fatigue, deception or other similar psychological states of a subject. Moreover, the method and apparatus of the present invention can be utilized to evaluate a number of subjects in a relatively rapid manner without requiring the operator to have as much training as required to utilize conventional polygraph and MRI techniques.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
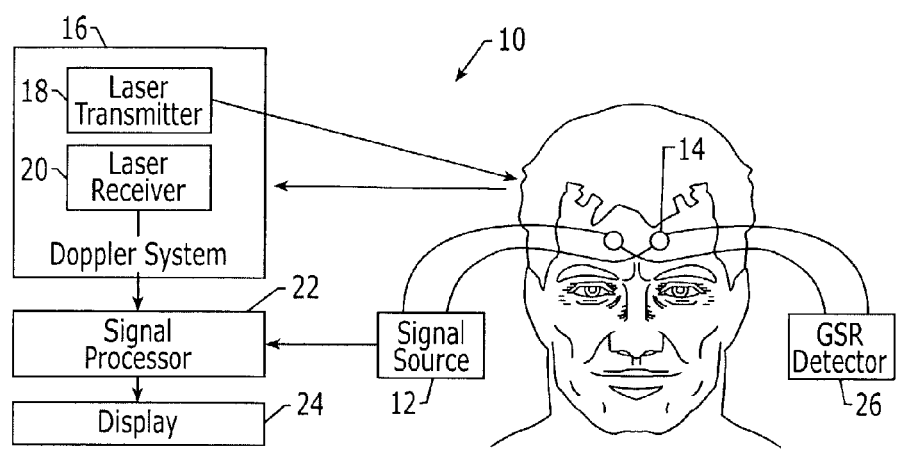
FIG. 1 is a schematic representation of an apparatus for detecting a tremor induced in the subject according to one embodiment of the present invention.

Referring now to FIG. 1, an apparatus 10 according to one embodiment to the present invention is depicted. As shown, the apparatus includes a signal source 12 for providing an excitation signal that is directly applied to the subject. In one embodiment, the signal source is an electrical signal source for providing an electrical stimulus to the subject, typically via electrodes 14 affixed to the subject, such as by a light adhesive or the like.

Figure 2:
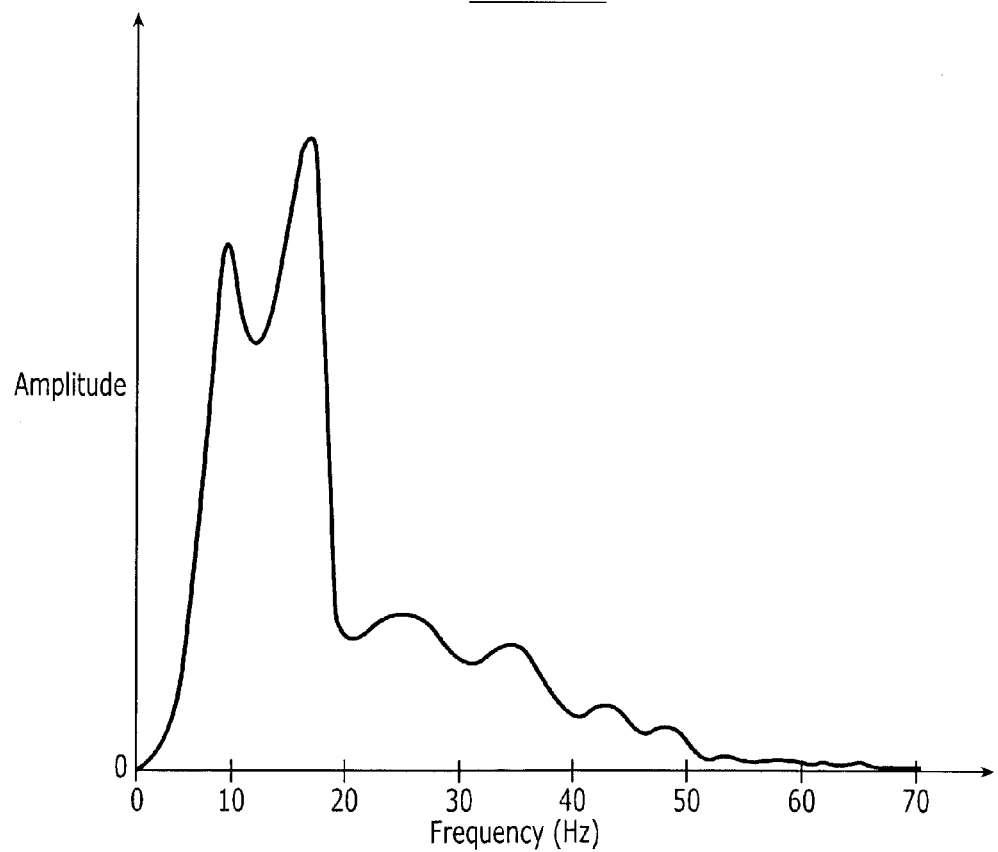
FIG. 2 is a graphical representation of a frequency spectrum of the tremor induced in the subject.

The signal source 12 generally provides an excitation signal having a predefined amplitude and frequency. In this regard, the amplitude and frequency of the excitation signal applied to the subject are generally selected so as to induce a tremor in the subject. Thus, the frequency of the excitation signal applied to the subject should generally be in the same range as the frequency of tremors that otherwise naturally occur within the muscle group to which the excitation signal is being applied in response to stress or another psychological state under investigation. As shown in FIG. 2, for example, the relative amplitude of a tremor present in the interosseous muscle over a frequency range of 0 to about 70 Hz is depicted. While the tremors supported by other muscle groups may vary in frequency somewhat, the tremors still are within the same general frequency range. Thus, the signal source typically provides an excitation signal having a frequency of no more than 100 Hz.

Moreover, the signal source 12 generally provides an excitation signal having a relatively small amplitude. In instances in which the signal source is an electrical signal source for providing an electrical stimulus to the subject, the amplitude of the electrical stimulus is generally within the range of 1 volt to 20 volts. In this regard, the amplitude of the electrical stimulus is preferably large enough to induce sufficient current within the subject to affect the muscle group of interest, while being small enough so as not to cause discomfort to the subject. Additionally, the excitation signal provided by the signal source is generally bipolar, such as an electrical stimulus consisting of a sinusoidal alternating current, to avoid otherwise polarizing the electrodes 14.

The excitation signal may be applied to various muscle groups and/or the associated neuronal innervations of the subject. As shown in FIG. 1, for example, the excitation signal may be applied via electrodes 14 to the muscles of the forehead of a subject, such as the Frontalis, the obicularis oculi and the corrugator supercilii and/or the associated neuronal innervations. However, the excitation signals may be applied to other muscle groups of the subject if so desired. For example, the excitation signal may be applied to muscles of the hand including the Adductor pollicis (brevis, obliquus and transversus) and/or the associated neuronal innervations.

According to the present invention, the tremor induced in the subject is then monitored. In this regard, the apparatus 10 of the present invention includes a Doppler system 16 for monitoring the tremor induced in the subject. The Doppler system can advantageously be a laser Doppler system having a laser transmitter 18 for providing electromagnetic radiation to irradiate the subject and, in particular, to irradiate at least that portion of the subject in which the tremor is induced, and a laser receiver 20 for receiving electromagnetic radiation returning in a modulated form from the subject. Further details regarding the laser Doppler system that may be utilized by the apparatus of the present invention are provided by U.S. Pat. No. 5,847,816 to Mark S. Zediker et al. and U.S. Pat. No. 5,867,257 to Robert R. Rice et al., the contents of both of which are incorporated herein by reference in their entirety.

The muscle tremor that has been induced in the subject modulates the electromagnetic radiation that is incident thereupon. Thus, the returning electromagnetic radiation that is detected by the laser receiver 20 has been modulated relative to the electromagnetic radiation that is provided by the laser transmitter 18.

As the subject experiences stress, emotion, fatigue, deception or other comparable psychological states, the amplitude and phase of the tremor induced in the subject will change in a deterministic manner. Thus, the apparatus 10 of the present invention may also analyze the returning electromagnetic radiation to determine the amplitude of the induced tremor and/or the phase shift of the induced tremor relative to the excitation signal provided by the signal source 12. Thus, the apparatus of the present invention may also include a signal processor 22, such as a microprocessor, a personal computer or other computing device, for analyzing the returning electromagnetic radiation. As schematically depicted in FIG. 1, the signal processor receives signals representative of both the modulated electromagnetic radiation detected by the laser receiver 20 and signals representative of the excitation signal provided by the signal source to the subject. Accordingly, the signal processor can determine the amplitude of the induced tremor and/or the phase shift of the induced tremor relative to the excitation signal applied to the subject.

As shown in FIG. 1, the signal processor 22 may be distinct from the laser receiver 20. However, the signal processor may, instead, be partially or completely embodied by the laser receiver 20 in other embodiments. In embodiments in which the analysis of the returning electromagnetic radiation includes an analysis of its phase shift relative to the phase of the excitation signals applied to the subject, the laser receiver may include a phase sensitive receiver for detecting the phase shift of the induced tremor relative to the excitation signal provided by the signal source 12. In this regard, the phase sensitive detector may include a phase locked loop for phase locking the excitation signal provided by the signal source to the modulated return signal.

By analyzing the amplitude and/or phase shift of the induced tremor, the signal processor 22 can provide information indicative of the stress, emotion, fatigue, deception or other similar psychological state of the subject. In this regard, the amplitude of the tremor induced in the subject and/or the phase shift of the tremor induced in the subject relative the excitation signal applied to the subject generally change in a deterministic manner as the subject is subjected to stress, emotion, fatigue, deception or other similar psychological states. Additionally, it is anticipated that the amplitude and/or the phase shift of the tremor induced in the subject will change in somewhat different manners or in somewhat different degrees in instances in which the subject is experiencing different emotional states. As such, the particular emotional state of the subject may be discerned from the analysis of the amplitude and/or phase shift of the induced tremor. For example, the amplitude of the tremor may differ in instances in which the subject is lying relative to instances in which the subject is fatigued. Additionally, the amplitude of the induced tremor may vary based upon the blood chemistry including the catecholamine levels of the subject. For example, the amplitude of a tremor in long voluntary muscles is likely to increase with increasing anxiety as reflected by increased levels of norepinephrine circulating in the blood stream.

The changes in the amplitude and/or phase shift of the induced tremor as the subject experiences different psychological states or varying degrees of the same psychological state may occur in response to or be most pronounced in response to excitation signals having a particular frequency depending upon the psychological state of interest and the individual subject. For example, the amplitude and/or phase shift of the induced tremor may be most pronounced in response to the application of excitation signals at a first frequency in instances in which the subject has one psychological state, while being most pronounced in response to the application of excitation signals at a second frequency in instances in which the subject has a different psychological state. The particular frequency of most interest may vary between subjects and may vary for a single subject as the blood chemistry of the subject varies. Thus, the signal source 12 may provide an excitation signal having a controllably adjustable frequency, thereby permitting the frequency of the excitation signal to be swept across a range of frequencies, such as from 0 Hz to about 100 Hz. While the frequency of the excitation signals is swept through the predefined range, the subject may be continually or repeatedly irradiated with electromagnetic radiation such that the returning modulated electromagnetic radiation that is detected has been generated in response to the application of excitation signals having a variety of different frequencies to the subject.

The information regarding the amplitude and/or phase shift of the induced tremor that is produced by the signal processor 22 may be stored for subsequent analysis. Additionally, or alternatively, the apparatus 10 may include a display 24 driven by the signal processor that presents images of the amplitude and/or phase shift of the induced tremor. As such, an operator can view the display, such as during questioning of the subject, to determine the veracity of the responses provided by the subject or to otherwise obtain the information regarding the psychological state of the subject.

Figure 3:
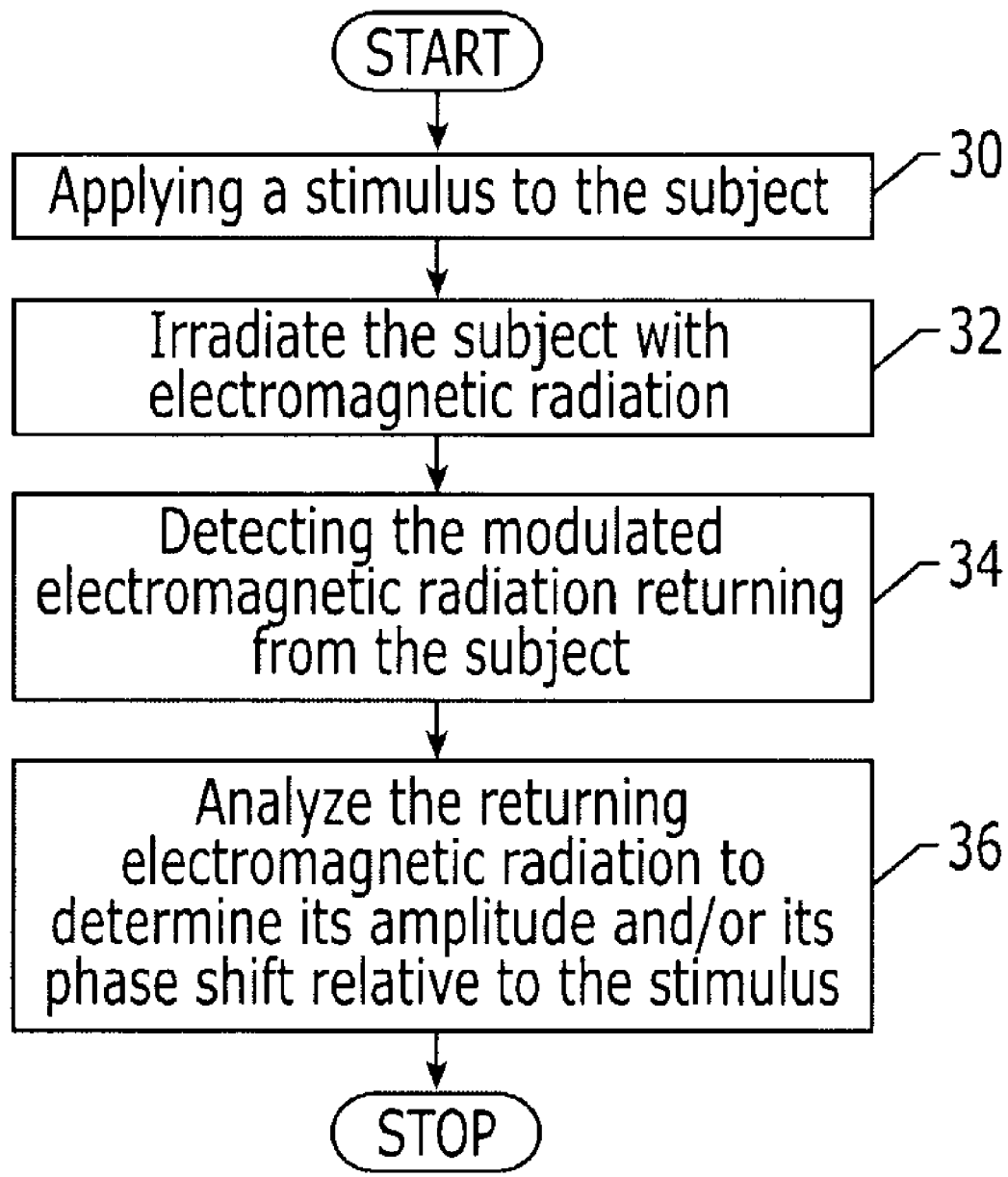
FIG. 3 is a flow chart illustrating the operations performed in accordance with the method and apparatus of one embodiment of the present invention.

As set forth by FIG. 3, the method and apparatus 10 of one embodiment to the present invention therefore operate by applying excitation signals, such as an electrical stimulus, to a subject to induce a tremor. See step 30. The subject is also irradiated with electromagnetic radiation, such as produced by a laser transmitter 18, while the tremor continues to be induced. See step 32. The electromagnetic radiation is detected, typically by a laser receiver 20, upon its return from the subject following modulation by the induced tremor. See step 34. The electromagnetic radiation that has been detected is then analyzed, such as by a signal processor 22. In this regard, the amplitude and/or phase shift of the induced tremor is generally analyzed relative to the excitation signal applied to the subject. See step 36. While this process may be conducted for excitation signals having a single frequency, excitation signals may be applied to the subject that have a frequency that is swept across a predefined range as described above, with the amplitude and/or phase shift of the induced tremor being detected in response to the application of excitation signals having a plurality of frequencies.

Since changes in the amplitude and/or phase shift of the induced tremor relate to the psychological state of the subject in a deterministic manner, the amplitude and/or phase shift of the induced tremor can be evaluated to determine the psychological state of the subject and to identify changes therein. Thus, the apparatus 10 and method of the present invention may be utilized by an operator in a variety of applications. For example, the apparatus and method of the present invention may operate in a comparable fashion to a polygraph with the operator quizzing the subject about a variety of topics and monitoring the amplitude and/or phase shift of the induced tremor in the subject as the subject formulates responses to the various queries. Since the amplitude and/or phase shift of the induced tremor is indicative of the psychological state of the subject, an analysis of the amplitude and/or phase shift of the induced tremor can detect instances in which the subject is lying or otherwise attempting to deceive the operator. Similarly, the method and apparatus of the present invention may be utilized to monitor the psychological state of a subject who is performing a critical function, such as an air traffic controller or another individual involved in flight operations. By monitoring the amplitude and/or phase shift of the induced tremor, an operator can detect instances in which the subject is becoming fatigued, such that appropriate replacements or assistance can be timely provided to the subject. Still further, the method and apparatus of the present invention may be utilized to screen subjects. In this regard, the subjects may be passengers of an aircraft who are screened to detect passengers who are have heightened stress levels or otherwise appear deceptive by again analyzing the amplitude and/or phase shift of the induced tremor, thereby permitting security personnel to further question a select group of the passengers in order to identify any passengers that may pose a threat to the safety of the aircraft or to its passengers.

While the actual magnitude of the amplitude and/or phase shift of the induced tremor is informative regarding the psychological state of the subject, the change in the amplitude and/or phase shift of the induced tremor is also of value as these changes are indicative of corresponding changes in the psychological state of the subject. Thus, the apparatus 10 and, most commonly, the signal processor 22 may be configured to compare the returning electromagnetic radiation and, in particular, the amplitude and/or phase shift of the induced tremor represented by the modulated electromagnetic radiation to a pre-established baseline. As such, the apparatus and method of the present invention, and, in particular, the signal processor can detect meaningful variations in the amplitude and/or phase shift of the induced tremor from the pre-established baseline. These meaningful variations may, in turn, be indicative of corresponding changes in the psychological state of the subject.

In order to supplement the information obtained regarding the psychological state of the subject from the modulated electromagnetic radiation, the apparatus 10 may also include a detector 20 in electrical communication with the electrodes 14 for determining the GSR of the subject. As know to those skilled in the art, the perspiration on the surface of the skin generally increases in instances in which the subject is lying or otherwise being deceptive, thereby bringing about a corresponding decrease in the electrical resistance that may be discerned by the GSR detector. By also monitoring the GSR, additional information regarding the psychological state of the subject may be therefore collected and analyzed.

As such, the method and apparatus 10 of the present invention permit a tremor that is induced in a subject to be detected and, based upon the amplitude and/or phase shift of the tremor, information regarding the psychological state of the subject may be obtained in a reliable and rapid manner. Moreover, the method and apparatus of the present invention can obtain information regarding the psychological state of the subject in a manner that is cost effective and relatively non-invasive and that does not require a highly skilled operator to administer and/or to interpret the results.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of detecting a tremor induced in a subject comprising:

applying electrical stimulus of a predefined frequency to the subject to thereby induce the tremor, wherein applying the electrical stimulus comprises selecting the predefined frequency based upon a frequency of tremors that otherwise occur naturally within a muscle group of the subject in response to stress or another psychological state and sweeping the predefined frequency of the electrical stimulus through a range of said predefined frequencies;

repeatedly irradiating the subject with electromagnetic radiation while the predefined frequency of the electrical stimulus that is applied to the subject is swept through the range of said predefined frequencies;

detecting the electromagnetic radiation returning from the subject following modulation by the induced tremor; and analyzing the returning electromagnetic radiation to thereby monitor the induced tremor.

2. A method according to claim 1 wherein analyzing the returning electromagnetic radiation comprises determining a phase shift of the induced tremor relative to the electrical stimulus applied to the subject.

3. A method according to claim 1 wherein detecting the returning electromagnetic radiation comprises detecting an amplitude of the returning electromagnetic radiation.

4. A method according to claim 1 wherein applying the electrical stimulus comprises applying an electrical stimulus having a predefined amplitude and frequency.

5. A method according to claim 4 wherein applying the electrical stimulus further comprises applying an electrical stimulus having a frequency of no more than 100 Hz.

6. A method according to claim 1 wherein analyzing the returning electromagnetic radiation comprises comparing the returning electromagnetic radiation to a preestablished baseline.

7. A method according to claim 1 further comprising determining a galvanic skin response of the subject.

* * * * *